United States Patent
Nalam et al.

(10) Patent No.: US 10,850,389 B2
(45) Date of Patent: Dec. 1, 2020

(54) SYSTEMS AND METHODS FOR A MULTI-AXIS ROBOTIC PLATFORM FOR STUDYING NEUROMECHANICS OF AN ANKLE JOINT

(71) Applicants: Varun Nalam, Tempe, AZ (US);
Hyunglae Lee, Phoenix, AZ (US)

(72) Inventors: Varun Nalam, Tempe, AZ (US);
Hyunglae Lee, Phoenix, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 0 days.

(21) Appl. No.: 15/993,527

(22) Filed: May 30, 2018

(65) Prior Publication Data

US 2018/0345482 A1   Dec. 6, 2018

Related U.S. Application Data

(60) Provisional application No. 62/512,507, filed on May 30, 2017.

(51) Int. Cl.
*A61B 5/11* (2006.01)
*A63B 23/08* (2006.01)
(Continued)

(52) U.S. Cl.
CPC ........... *B25J 9/0009* (2013.01); *A61B 5/1121* (2013.01); *A61B 5/4528* (2013.01); *B25J 9/1664* (2013.01);
(Continued)

(58) Field of Classification Search
CPC ....... A61B 5/0488; A61B 5/11; A61B 5/1121; A61B 5/4528; A63B 23/00; A63B 23/08;
(Continued)

(56) References Cited

U.S. PATENT DOCUMENTS 4,306,714 A * 12/1981 Loomis ................. A63B 23/08
482/131
4,650,183 A * 3/1987 McIntyre ............... A63B 23/08
482/112
(Continued)

FOREIGN PATENT DOCUMENTS

CN  203130824 U   8/2013
KR  101661534 B1  9/2016
(Continued)

OTHER PUBLICATIONS

International Search Report and Written Opinion issued in corresponding PCT Patent Application No. PCT/US18/35157, dated Aug. 28, 2018, 10 pages.
(Continued)

*Primary Examiner* — Nguyen Q. Ha
(74) *Attorney, Agent, or Firm* — Polsinelli PC

(57) ABSTRACT

A multi-axis robotic platform for studying neuromechanics comprises a bottom plate, a middle plate, and a top plate is disclosed herein. The middle plate is movably coupled between the bottom plate and the top plate. The top plate comprises a support surface for receiving an ankle. A first actuator is disposed upon the bottom plate and is connected to the middle plate via a first coupling such that a shaft of the first actuator rotates the middle plate along a dorsiflexion-plantarflexion (DP) axis of the ankle. A second actuator is disposed upon the middle plate and is connected to the top plate via a second coupling such that a shaft of the second actuator rotates the top plate along an inversion-eversion (IE) axis of the ankle. The multi-axis robotic platform can analyze ankle impedance and reflex characteristics in two degrees-of-freedom (DP movement and IE movement) during postural and locomotion tasks.

15 Claims, 8 Drawing Sheets

(51) Int. Cl.
B25J 9/00 (2006.01)
B25J 9/16 (2006.01)
B25J 19/02 (2006.01)
A61B 5/00 (2006.01)
A61B 5/0488 (2006.01)

(52) U.S. Cl.
CPC .............. *B25J 9/1694* (2013.01); *B25J 19/02* (2013.01); *A61B 5/0488* (2013.01); *Y10S 901/09* (2013.01); *Y10S 901/46* (2013.01)

(58) Field of Classification Search
CPC . B25J 9/00; B25J 9/0009; B25J 9/1664; B25J 9/1694; B25J 19/02; Y10S 901/09; Y10S 901/46

See application file for complete search history.

(56) References Cited

U.S. PATENT DOCUMENTS

| | | | |
|---|---|---|---|
| 4,733,859 A * | 3/1988 | Kock | A63B 23/025 482/127 |
| 8,206,267 B2 | 6/2012 | Holden et al. | |
| 8,636,627 B2 * | 1/2014 | Zhang | A61B 5/1124 482/52 |
| 2005/0239611 A1 * | 10/2005 | Commisso | A61H 1/0266 482/93 |
| 2009/0259338 A1 * | 10/2009 | Tong | A63B 23/0355 700/258 |
| 2011/0256983 A1 * | 10/2011 | Malack | A63B 23/0405 482/4 |
| 2011/0306473 A1 * | 12/2011 | Saglia | A61H 1/0266 482/79 |
| 2014/0378876 A1 | 12/2014 | Malosio et al. | |
| 2017/0340918 A1 * | 11/2017 | Walker | A63B 21/4049 |
| 2019/0076696 A1 * | 3/2019 | Townsend | A63B 23/03541 |
| 2019/0160653 A1 | 5/2019 | Aremiadis et al. | |
| 2019/0217465 A1 | 7/2019 | Artemiadis et al. | |
| 2019/0314987 A1 | 10/2019 | Hunt et al. | |

FOREIGN PATENT DOCUMENTS

| | | |
|---|---|---|
| KR | 20170041545 A | 4/2017 |
| WO | 2014/085732 A1 | 6/2014 |
| WO | 2018022689 A1 | 2/2018 |
| WO | 2018022692 A1 | 2/2018 |

OTHER PUBLICATIONS

Burdet et al., "Human Robotics: Neuromechanics and Motor Control," Human Robotics: Neuromechanics and Motor Control, pp. 1-277, 2013.
Scheid, 1968, Schaum' s Outline of Theory and Problems of Numerical Analysis, McGraw-Hill, New York.
Antonsson et al., 1985. "The frequency content of gait". Journal of biomechanics, 18(1), pp. 39-47.
Andersen et al., 1995, "An Actuator System for Investigating Electrophysiological and Biomechanical Features Around Human Ankle Joint During Gait," IEEE Trans. Rehabil. Eng., 3(4), pp. 299-306.
Arndt et al., "Intrinsic foot kinematics measured in vivo during the stance phase of slow running," J. Biomech., vol. 40, pp. 2672-2678, 2007.
Au et al., "Biomechanical Design of a Powered Ankle-Foot Prosthesis," Proceedings of 2007 IEEE 10th International on Rehabilitation Robotics, pp. 298-303.
Au et al., 2008, "On the Design of a Powered Ankle-Foot Prosthesis. The Importance of Series and Parallel Motor Elasticity," Rob. Autom. Mag, 15(3), pp. 52-59.
Bennett et al., "Time-Varying Stiffness of Human Elbow Joint During Cyclic Voluntary Movement," Exp. Brain Res., 88 (2), pp. 433-442, 1991.

Buerger et al., "Complementary stability and loop shaping for improved human-robot interaction," IEEE Transactions on Robotics, vol. 23, pp. 232-244, Apr. 2007.
Cain et al., 2007, "Locomotor Adaptation to a Pow-ered Ankle-Foot Orthosis Depends on Control Method," J. Neuroengineering Rehabil., 4(1), p. 48.
Casadio et al., 2005, "Direct Measurement of Ankle Stiffness During Quiet Standing: Implications for Control Modelling and Clinical Application," Gait and Posture, 21(4), pp. 410-424.
Chagdes et al., "Dynamic stability of a human standing on a balance board," J Biomech, vol. 46, pp. 2593-602, Oct. 18 2013.
Clauser, Weight, Volume, and Center of Mass of Segments of the Human Body. Springfield, VA, USA: Nat. Tech. Inf. Service, 1969.
Davis et al., "Gait characterization via dynamic joint stiffness," Gait Posture, vol. 4, pp. 224-231, 1996.
Farris et al., "The mechanics and energetics of human walking and running: a joint level perspective," Journal of The Royal Society Interface, p. rsif20110182, 2011.
Ferris et al., 1999. "Runners adjust leg stiffness for their first step on a new running surface". Journal of biomechanics, 32(8), pp. 787-794.
Ficanha et al., "Ankle mechanics during sidestep cutting implicates need for 2-degrees of freedom powered ankle-foot prostheses," J. Rehabil. Res. Dev, vol. 52, pp. 97-112, 2015.
Ficanha et al., "Instrumented Walkway for Estimation of the Ankle Impedance in Dorsiflexion-Plantarflexion and Inversion-Eversion during Standing and Walking," Proceedings of the ASME Dynamic Systems and Control Conference, 2015.
Ficanha, 2015. "Anthropomorphic robotic ankle-foot prosthesis with active dorsiflexion-plantarflexion and inversion-eversion".
Finley et al., 2013. "Acceleration dependence and task-specific modulation of short-and medium-latency reflexes in the ankle extensors". Physiological reports, 1(3), p. e00051.
Fitzpatrick et al., "Ankle stiffness of standing humans in response to imperceptible perturbation: Reflex and task-dependent components," J. Physiol., vol. 454, pp. 533-547,1992.
Gomi et al., 1997, "Human Arm Stiffness and Equilibrium-Point Trajectory During Multi-Joint Movement," Biol. Cyberri., 76(3), pp. 163-171.
Gordon et al., 2006, "Mechanical Performance of Artificial Pneumatic Muscles to Power an Ankle-Foot Orthosis," J. Biomech., 39(10), pp. 1832-1841.
Gordon et al., 2007, "Learning to Walk With a Robotic Ankle Exoskeleton," J. Biomech., 40(12), pp. 2636-2644.
Harlaar et al., "Passive stiffness characteristics of ankle plantar flexors in hemiplegia," Clin. Biomech., vol. 15, pp. 261-270, 2000.
Hitt et al., "An active foot-ankle prosthesis with biomechanical energy regeneration," J. Med. Devices, vol. 4, pp. 011003-1-011003-9, 2010.
Hitt et al., "Bionic running for unilateral transtibial military amputees," presented at the 27th Army Sci. Conf., Orlando, FL, USA, 2010.
Hogan, "The Mechanics of Multi-Joint Posture and Movement Control," Biological Cybernetics, vol. 52, pp. 315-331, 1985.
Houdijk et al., 2008. "Joint stiffness of the ankle during walking after successful mobile-bearing total ankle Gait & posture, 27(1), pp. 115-119. replacement".
Hunter et al., "Dynamics of human ankle stiffness: Variation with mean ankle torque," J. Biomech., vol. 15, pp. 742-752, 1982.
Kearney et al., "Dynamics of human ankle stiffness: Variation with displacement amplitude," J. Biomech., vol. 15, pp. 753-756,1982.
Kearney et al., "Identification of intrinsic and reflex contributions to human ankle stiffness dynamics," IEEE Trans. Biomed. Eng., vol. 44, No. 6, pp. 493-504, Jun. 1997.
Kearney et al., "System identification of human joint dynamics," Critical reviews in biomedical engineering, vol. 18, pp. 55-87, 1989.
Kearney et al., "System identification of stretch reflex dynamics," Crit. Rev. Biomed. Eng., vol. 18, pp. 55-87,1990.
Kerdok et al., 2002. "Energetics and mechanics of human running on surfaces of different stiffnesses". Journal of Applied Physiology, 92(2), pp. 469-478.

(56) References Cited

OTHER PUBLICATIONS

Kirsch et al., "Identification of time-varying stiffness dynamics of the human ankle joint during an imposed movement," Exp. Brain Res., vol. 114, pp. 71-85,1997.
Lamontagne et al., "Viscoelastic behavior of plantar flexor muscle-tendon unit at rest," J. Ortho. Sports Phys. Therapy, vol. 26, pp. 244-252,1997.
Lee et al., "Essential considerations for design and control of human-interactive robots," in in Proc. 2016 IEEE International Conference on Robotics and Automation (ICRA 2016), Stockholm, 2016, pp. 3069-3074.
Lee et al., "Multivariable Dynamic Ankle Mechanical Impedance with Active Muscles," IEEE Transactions on Neural Systems and Rehabilitation Engineering, vol. 22, pp. 971-981, 2014.
Lee et al., "Multivariable Static Ankle Mechanical Impedance with Active Muscles," IEEE Transactions on Neural Systems and Rehabilitation Engineering, vol. 22, pp. 44-52, Jan. 2014.
Lee et al., 2014. "Multivariable dynamic ankle mechanical impedance with relaxed muscles". Neural Systems and Rehabilitation Engineering, IEEE Transactions on, 22(6), pp. 1104-1114.
Lee et al., 2011. "Multivariable static ankle mechanical impedance with relaxed muscles". Journal of biomechanics, 44 (10), pp. 1901-1908.
Lee et al., "Summary of human ankle mechanical impedance during walking," IEEE Journal of Translational Engineering in Health and Medicine, vol. 4, 2016.
Lee et al., "Time-varying ankle mechanical impedance during human locomotion," IEEE Trans Neural Syst. Rehabil. Eng., vol. 23, No. 5, pp. 755-764, Sep. 2015.
Loram et al., 2002, "Direct Measurement of Human Ankle Stiffness During Quiet Standing: The Intrinsic Mechanical Stiffness is Insufficient for Stability," J. Physiol., 545(3), pp. 1041-1053.
Lortie et al., "Identification of physiological systems: Estimation of linear time varying dynamics with non-white inputs and noisy outputs," Med. Biol. Eng. Comput., vol. 39, pp. 381-390,2001.
Ludvig et al., 2011. "Identification of time-varying intrinsic and reflex joint stiffness". Biomedical Engineering, IEEE Trans-actions on, 58(6), pp. 1715-1723.
Macneil et al., 1992, "Identification of Time-Varying Biological Systems From Ensemble Data (Joint Dynamics Application)," IEEE Trans. Biomed. Eng., 39(12), pp. 1213-1225.
Mirbagheri et al., "Intrinsic and reflex contributions to human ankle stiffness: variation with activation level and position," Experimental Brain Research, vol. 135, pp. 423-436, 2000.
Mirbagheri et al., "Quantitative, objective measurement of ankle dynamic stiffness: infra-subject reliability and intersubject variability," presented at the 18th Annu. Int. Conf. IEEE Eng. Med. Biology Soc., Amsterdam, The Netherlands, 1996.
Morasso et al., "Ankle muscle stiffness alone cannot stabilize balance during quiet standing," J. Neurophysiol., vol. 88, pp. 2157-2162, 2002.
Morier et al., 1990, "Low Inertia, Rigid Limb Fixation Using Glass Fibre Casting Bandage," Med. Biol. Eng. Comput., 28 (1), pp. 96-99.
Noel et al., 2009, "Using an Electrohydraulic Ankle Foot Orthosis to Study Modifications in Feedforward Control During Locomotor Adaptation to Force Fields Applied in Stance," J. Neuroeng. Rehabil., 6(1), p. 16.
Orendurff et al., "The kinematics and kinetics of turning: Limb asymmetries associated with walking a circular path," Gait Posture, vol. 23, pp. 106-111, 2006.
Palmer, "Sagittal plane characterization of normal human ankle function across a range of walking gait speeds," M.S. thesis, Dept. Mech. Eng., Mass. Inst. Technol., Cambridge, MA, USA, 2002.
Patane et al., "A 3-DOF parallel robot with spherical motion for the rehabilitation and evaluation of balance performance," IEEE Trans-actions on Neural Systems and Rehabilitation Engineering, vol. 19, pp. 157-166, 2011.
Perreault et al., "Considering Limb Impedance in the Design and Control of Prosthetic Devices," In Neuro-robotics: From Brain Machine Interfaces to Rehabilitation Robotics, Panagiotis K. Artemiadis (Ed.), ed: Springer, 2014.
Perreault et al., "Multijoint Dynamics and Postural Stability of the Human Arm," Exp. Brain Res., 157(4), pp. 507-517. Au, S., and Hen•, H., 2008, "On the Design of a Powered Ankle-Foot Prosthesis. The Importance of Series and Parallel Motor Elasticity," IEEE Rob. Autom. Mag., 15(3), pp. 52-59.
Perreault et al., "Multiple-Input, Multiple-Output System Identification for Characterization of Limb Stiffness Dynamics," Biol. Cybem., 80(5), pp. 327-337, 1998.
Popescu et al., "Elbow Impedance During Goal-Directed Movements," Exp. Brain Res., 152(1), pp. 17-28, 2003.
Rastgaar et al., "Multi-directional dynamic mechanical impedance of the human ankle; A key to anthropomorphism in lower extremity assistive robots," in Neuro-Robotics, vol. 2, Artemiadis, Berlin, Germany: Springer-Veralg, 2014, pp. 157-178.
Rouse et al., "Development of a mechatronic platform and validation of methods for estimating ankle stiffness during the stance phase of walking," J. Biomech. Eng., vol. 135, pp. 10091-10098, 2013.
Rouse et al., "Estimation of human ankle impedance during the stance phase of walking," IEEE Trans. Neural Syst. Rehabil. Eng., vol. 22, No. 4, pp. 870-878, Jul. 2014.
Rouse et al., "The difference between stiffness and quasi-stiffness in the context of biomechanical modeling," IEEE Transactions on Biomedical Engineering, vol. 60, pp. 562-568, 2013.
Rouse et al., 2012, "Validation of Methods for Determining Ankle Stiffness During Walking Using the Perturberator Robot," Proceedings of the IEEE International Conference on Biomedi-cal Robotics and Biomechatronics, pp. 1650-1655.
Roy et al., 2007, "Measurement of Human Ankle Stiffness Using the Anklebot," IEEE 10th International Conference, Rehabilitation Robotics, 2007, ICORR, MIT, Cambridge, MA, Jun. 13-15, pp. 356-363.
Roy et al., 2009, "Robot-Aided Neurorehabilitation: A Novel Robot for Ankle Rehabilitation," IEEE Trans. Robotics, 25 (3), pp. 569-582.
Rydahl et al., "Ankle stiffness and tissue compliance in stroke survivors: A validation of myotonometer measurements," Arch. Phys. Med. Rehabil., vol. 85, pp. 1631-1637, 2004.
Sancisi et al., "Validation of a one degree-of-freedom spherical model for kinematics analysis of the human ankle joint," J. Foot Ankle Res., vol. 5, pp. 1-2, 2012.
Sancisi et al., "One-degree-of-freedom spherical model for the passive motion of the human ankle joint," Med. Biol. Eng. Comput., vol. 52, pp. 363-373, 2014.
Saripalli et al., "Dynamic ankle stability and ankle orientation," presented at the 7th Symp. Footwear Biomechanics Conf., Cleveland, OH, USA, 2005.
Sasagawa et al., "Balance control under different passive contributions of the ankle extensors: Quiet standing on inclined surfaces," Exp. Brain Res., vol. 196, pp. 537-544, 2009.
Selen et al., "Impedance is Modulated to Meet Accuracy Demands During Goal-Directed Arm Movements," Exp. Brain Res., 172(1), pp. 129-138. 2005.
Shamaei et al., "Estimation of quasi-stiffness and propulsive work of the human ankle in the stance phase of walking," PLoS One, vol. 8, e59935, pp. 1-12, 2013.
Singer et al., 1995. "Parameter estimation for a prosthetic ankle". Annals of biomedical engineering, 23(5), pp. 691-696.
Sinkjaer et al., "Muscle stiffness in human ankle dorsiflexors: Intrinsic and reflex components," J. Neurophysiol., vol. 60, pp. 1110-1121, 1998.
Sup et al., "Design and control of a powered transfemoral prosthesis," Int. J. Robot. Res., vol. 27, pp. 263-273, 2008.
Sup, "A powered self-contained knee and ankle prosthesis for near normal gait in transfemoral amputees," Ph.D. dissertation, Dept. Mech. Eng., Vanderbilt Univ., Nashville, TN, USA, 2009.
Weiss et al., "Position dependence of ankle joint dynamics—I. Passive mechanics," Journal of biomechanics, vol. 19, pp. 727-735, 1986.

(56) References Cited

OTHER PUBLICATIONS

Weiss et al., "Position dependence of ankle joint dynamics—II. Active mechanics," Journal of biomechanics, vol. 19, pp. 737-751, 1986.
Wells, 1981, "The Projection of the Ground Reaction Force as a Predictor of Internal Joint Moments," Bull. Prosthet. Res., 10, pp. 15-19.
Winter et al., "Ankle muscle stiffness in the control of balance during quiet standing," J. Neurophysiol., vol. 85, pp. 2630-2633, 2001.
Winter, "Energy Generation and Absorption at the Ankle and Knee during Fast, Natural, and Slow Cadences," Clinical Orthopaedics and Related Research, pp. 147-154, 1983.
Xu et al., 1991, "An Airjet Actuator System for Identification of the Human Arm Joint Mechanical Properties," IEEE Trans. Biomed. Eng., 38(11), pp. 1111-1122.
Zinder et al., "Validity and reliability of a new in vivo ankle stiffness measurement device," J. Biomech., vol. 40, pp. 463-467, 2007.
Ficanha, E. et al., "Design and Evaluation of a 2-DOF Instrumented Platform for Estimation of the Ankle Mechanical Impedance in the Sagittal and Frontal Planes", IEEE/ASME Transactions on Mechatronics, Oct. 2016 (Date of Publication: Apr. 8, 2016), vol. 21, No. 5, pp. 2531-2542 <DOI:10.1109/TMECH.2016.2552406>.
Nalam, V. et al., "Design and validation of a multi-axis robotic platform for the characterization of ankle neuromechanics", 2017 IEEE International Conference on Robotics and Automation (Singapore, Singapore, May 29-Jun. 3, 2017), 2017 (Date Added to IEEE Xplore: Jul. 24, 2017), pp. 511-516 <DOI:10.1109/ICRA.2017.7989064>.
Nalam, V. et al., "Development of a Multiple Axis Robotic Platform for Ankle Studies", ASME 2016 Dynamic Systems and Control Conference (Minneapolis, Mn, Oct. 12-24, 2016), 2016 (available online Feb. 2017), No. DSCC2016-9893, 6 pages <DOI:10.1115/DSCC2016-9893>.
Nalam, V. et al., "Robotic Approach to Characterize Altered Ankle Mechanics Affected by Stroke and Multiple Sclerosis", 42nd Annual Meeting of the American Society of Biomechanics (Rochester, MN, Aug. 8-11, 2018), 2018, 2 pages.
Rouse, E. et al., "Development of a Mechatronic Platform and Validation of Methods for Estimating Ankle Stiffness During the Stance Phase of Walking", Journal of Biomechanical Engineering, Aug. 2013, vol. 135, No. 8, article 081009, 8 pages <DOI:10.1115/1.4024286>.
Sup, F. et al., "Self-Contained Powered Knee and Ankle Prosthesis: Initial Evaluation on a Transfemoral Amputee", 2009 IEEE International Conference on Rehabilitation Robotics (Kyoto, Japan, Jun. 23-26, 2009), 2009 (Date Added to IEEE Xplore: Aug. 21, 2009), pp. 638-644 <DOI:10.1109/ICORR.2009.5209625>.
Winter, D., "Human balance and posture control during standing and walking", Gait & Posture, Dec. 1995, vol. 3, No. 4, pp. 193-214 <DOI:10.1016/0966-6362(96)82849-9>.

* cited by examiner

SYSTEMS AND METHODS FOR A MULTI-AXIS ROBOTIC PLATFORM FOR STUDYING NEUROMECHANICS OF AN ANKLE JOINT

CROSS REFERENCE TO RELATED APPLICATIONS

This is a non-provisional application that claims benefit to U.S. provisional application Ser. No. 62/512,507, filed on May 30, 2017, which is incorporated by reference in its entirety.

FIELD

The present disclosure generally relates to a multi-axis robotic platform for studying neuromechanical interactions, and in particular relates to a multi-axis robotic platform for studying the neuromechanics of an ankle joint.

BACKGROUND

Studying the neuromuscular interactions of the ankle has been of high interest, as a successful study would have various important implications in both the healthcare and sports fields. Previous approaches have attempted to characterize the human ankle and ankle impedance, for example, by measuring quasi-stiffness of the ankle (torque-angle relationship at the ankle) during lower-extremity functions in a conventional gait lab.

However, quasi-stiffness is distinct from the mechanical impedance of a joint, and quasi-stiffness does not provide insight into dynamic properties of the joint. In attempts to directly measure ankle impedance, simple devices consisting of a servomotor and a cast supporting the leg have been used. However, their use has been strictly limited to static postures, mostly seated or supine.

Accordingly, it would be desirable to directly and accurately study the neuromuscular interactions of the ankle while it performs various functional tasks in a realistic simulated mechanical environment. It is with these observations in mind, among others, that various aspects of the present disclosure were conceived and developed.

DETAILED DESCRIPTION

Figure 1:
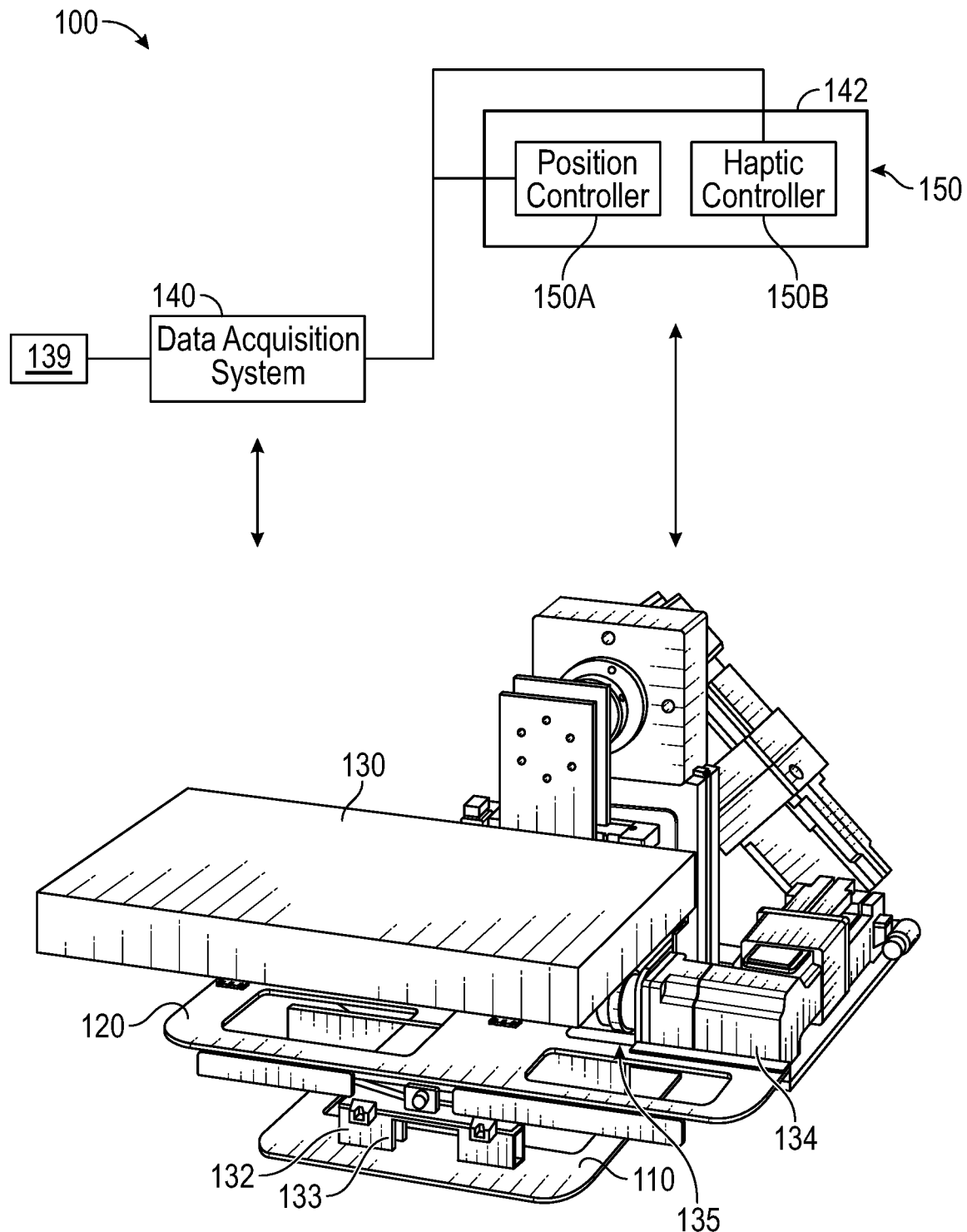
FIG. 1 is a schematic depiction of a multi-axis robotic platform, according to aspects of the present disclosure.

Human posture, balance, and locomotion involve complex dynamic interactions between humans and their surrounding physical environment. These interactions can be quantified by the fundamental mechanical property of mechanical impedance, which is the dynamic relationship between positions/angles and forces/torques at the limb or joint. Mechanical impedance can be decomposed into intrinsic impedance (arising from the mechanical properties of the joint, passive tissues, and active muscles) and reflex impedance (arising from the changes in muscle activation due to afferent response to muscle stretch). Humans perform various motor tasks by properly modulating both the intrinsic and reflexive components of the limb/joint mechanical impedance. Hence, refined characterization of the limb and joint impedances can aid in understanding human motor control during interactions with the physical environment, and can additionally aid in designing improved human machine interfaces and bio-inspired robots.

The human ankle is one of the most important joints in lower extremity functions, and is the primary point of interaction with the environment. It is vital for maintaining balance and providing the necessary power for propulsion, turning, and shock absorption during locomotion. Hence even trivial impairments to the ankle joint can significantly affect basic motor functions. Characterizing mechanical impedance and reflex characteristics of the ankle can provide improved insight into the neuromuscular mechanisms of the ankle joint, and can additionally aid in the design of lower-extremity wearable robots, including active ankle-foot orthoses, powered prosthesis, and exoskeletons.

Accordingly, disclosed herein is a multi-axis robotic platform for investigating the neuromechanics and neuromuscular properties of the ankle joint, including mechanical impedance and reflex characteristics of the ankle. In particular, the multi-axis robotic platform can characterize these properties in the sagittal and frontal planes and during the performance of various functional, postural and locomotion tasks.

Recalling that the mechanical impedance of the ankle joint is given by the dynamic relationship between the differential change in the angle or position of the ankle joint and the corresponding torque at the ankle joint, in the context of the present disclosure, the impedance and reflex characteristics of the ankle can be studied by applying position perturbations to the ankle and observing the corresponding torque responses at the ankle.

The disclosed multi-axis robotic platform can produce and apply such position perturbations to the ankle joint with high accuracy in both degrees of freedom, with angular speeds that can exceed 200°/s. The multi-axis robotic platform can emulate a wide range of haptic environments in two degrees-of-freedom (DOFs) of the ankle: dorsiflexion-plantarflexion (DP) in the sagittal plane and inversion-eversion (IE) in the frontal plane. On this basis, realistic mechanical environments can be seamlessly simulated and the ankle transiently perturbed for characterization of its neuromuscular properties. In some embodiments a torque of 400 Nm can be provided along the DP axis and a torque of 150 Nm can be provided along the IE axis, and a range of −20° to 20° can be covered in the sagittal plane and a range of −10° to 10° can be covered in the frontal plane.

The multi-axis robotic platform can be controlled via a position controller and a haptic controller, which in some embodiments can be switched between rapidly (e.g. less than 0.5 ms). In some embodiments, the position controller can achieve an accuracy of 0.05°, even when controlling actuators under loading conditions (e.g. a subject of 100 kg standing on the multi-axis robotic platform). In some embodiments, the haptic controller emulates a wide range of mechanical environments, from compliant to rigid (50-1000 Nm/rad), with an error of 2% of the commanded values, or less. In some embodiments, the disclosed multi-axis robotic platform can reliable estimate the stiffness of a human ankle mockup (17.8-171.0 Nm/rad) with an error of 1.6%, or less. In some embodiments, the disclosed multi-axis robotic platform can elicit medium-latency and long-latency reflex responses of the ankle muscles.

Platform Design

FIG. 1 depicts a perspective view of an exemplary multi-axis robotic platform 100, which can achieve one or more of the design and performance characteristics described above. For example, in some embodiments the multi-axis robotic platform 100 can be designed to provide perturbations for subjects weighing up to 100 kg, although other designed subject weights are possible without departing from the scope of the present disclosure.

As illustrated, platform 100 comprises three plates: a bottom plate 110, a middle plate 120, and a top plate 130. One or more of these plates (and one or more other components of platform 100) can be fabricated using a metal with a high rigidity and/or yield strength, which in some embodiments can be 1018 alloy steel. Additionally, in some embodiments the height from the bottom plate 110 to the top of platform 100 is 195 mm, although other heights can be utilized without departing from the scope of the present disclosure.

Platform 100 additionally comprises two actuators: a DP actuator (132) and an IE actuator (134). These actuators provide perturbations in the two degrees-of-freedom (DOFs) of platform 100, i.e. the DP actuator 132 provides dorsiflexion-plantarflexion (DP) in the sagittal plane and the IE actuator 134 provides inversion-eversion (IE) in the frontal plane.

Bottom plate 110 is fixed to or otherwise placed upon the ground or some other environmental surface and is configured to provide one or more support structures for middle plate 120 and top plate 130. Bottom plate 110 additionally supports the DP actuator 132 which provides platform 100 with motion along the DP axis/perturbations in the sagittal plane. In some embodiments, the DP actuator 132 is attached to bottom plate 110 such that the axis of rotation along the DP axis is aligned with the axis of rotation of the ankle. In other words, an output shaft of the DP actuator 132 aligns with the ankle axis when platform 100 is in use. The DP actuator 132 can be a servo or servomotor, and can be brushed or brushless. In some embodiments, the DP actuator could be an AKM43L brushless servomotor manufactured by Kollmorgen (VA), although other actuators and actuation mechanisms can be employed without departing from the scope of the present disclosure.

In the context of the illustrated multi-axis robotic platform 100, the DP actuator 132 can provide a maximum torque of 464.8 Nm and can be augmented by a gearhead with a gear ratio of 40:1, although other maximum torques and gearheads/gear ratios can be employed without departing from the scope of the present disclosure. In addition to being attached to bottom plate 110, the DP actuator 132 is connected to middle plate 120 via a coupling 133, which in some embodiments can be a KG220 coupling manufactured by GAM (IL). In some embodiments, the coupling 133 can be a flexible servo drive coupling, such as the Zeromax SCO6OR. Regardless of the specific choice of coupling, the coupling 133 acts to constrain middle plate 120 to rotate along the DP axis in the sagittal plane.

Middle plate 120 is coupled to bottom plate 110 via a set of rails (e.g. metal rails, which can be manufactured from a similar or identical material as bottom plate 110 and/or middle plate 120) which act to prevent or limit transverse loading of the output shaft of the DP actuator 132 connected between bottom plate 110 and middle plate 120. This set of rails additionally acts to support middle plate 120 as it is perturbed or rotated in the sagittal plane by the DP actuator 132. In some embodiments, one or more rollers can be provided between middle plate 120 and bottom plate 110, such that the rollers transmit the weight of a subject using platform 100 (and transmit the weight of the actuated part of platform 100) onto bottom plate 110. The one or more rollers can also act to prevent or limit transverse loading of the output shaft of the DP actuator 132.

Middle plate 120 further supports the IE actuator 134 which provides platform 100 with motion along the IE axis/perturbations in the frontal plane. The IE actuator 134 can be a servo or servomotor, and can be brushed or brushless. The IE actuator 134 and the DP actuator 132 can be non-identical, although it is also possible that the two actuators may be identical. In some embodiments, the IE actuator 134 could be an AKM33H brushless servomotor manufactured by Kollmorgen (VA), although other actuators and actuation mechanisms can be employed without departing from the scope of the present disclosure.

In the context of the illustrated multi-axis robotic platform 100, the IE actuator 134 can provide a maximum torque of 213.75 Nm and can be augmented by a gearhead with a gear ratio of 25:1, although other maximum torques and gearheads/gear ratios can be employed without departing from the scope of the present disclosure. In addition to being attached to middle plate 120, the IE actuator 134 is connected to top plate 130 via a high-speed rigid coupling 135, which in some embodiments can be a KG40 coupling manufactured by GAM (IL). This high-speed rigid coupling 135 constrains top plate 130 to rotate along the IE axis in the frontal plane.

Top plate 130 is attached to middle plate 120 (e.g. through a set of rails or other supports) and in operation of platform 100, supports the subject. The combined weight of top plate 130 and the subject is transmitted to middle plate 120 through one or more weight bearings, which prevent or limit transverse loading of the output shaft of the IE actuator 134. In some embodiments, the IE actuator 134 is attached between middle plate 120 and top plate 130 such that the axis of rotation in the frontal plane is below top plate 130 and does not coincide with the ankle axis for IE. Because top plate 130 can rotate in the frontal plane and middle plate 120 can rotate in the sagittal plane, platform 100 thus has two DOFs which can be controlled independently to provide perturbations to the ankle.

In order to obtain ankle torques for the estimation of mechanical impedance of the ankle, a force plate is attached to top plate 130. This force plate can also be utilized in the emulation of various mechanical environments, as will be later described. In some embodiments, the force plate can consist of four load cells distributed across the four corners of top plate 130. In operation of platform 100, the load cell signals can be processed and transmitted as eight channels of analog signals. The first four signals transmit an analog voltage proportional to the normal force acting on each of the load cells, and the last four signals transmit an analog voltage proportional to the shear force acting along the four edges of the top face of the force plate. In some embodiments, the force plate can be provided as model 926AA3 manufactured by Kistler (NY), although other force plates can be employed without departing from the scope of the present disclosure.

Data Acquisition

In order to successfully determine or otherwise characterize impedance and reflex characteristics of the ankle, platform 100 needs to acquire data relating to positions and torques at the ankle, along with data relating to muscle activations. These data can be obtained from various sensors (139) integrated with platform 100, although it is also possible that one or more of the sensors can be discrete or otherwise provided separate from platform 100, e.g. in the form of an external sensing or measuring unit.

Regardless of the specific physical configuration of the sensors and/or sensing hardware, a data acquisition system 140 is used to obtain the needed data. In a first example, the data acquisition system 140 can comprise a PCM 3356 processor equipped with a plurality of PC104 ports, and a PC104-compatible DAC, such as the DMM32-DX-AT manufactured by Diamond. The DMM32-DX-AT has 32 analog inputs and 4 analog outputs with 16-bit resolution and a maximum sample rate of 250 kHz. However, other control mechanisms, processors, data acquisition systems, and DACs may be employed without departing from the scope of the present disclosure e.g., in a second example, the data acquisition system 140 can comprise a computing device connected to an NI-PCiE 6343, 16-bit DAC.

The data acquisition system 140 obtains position data from respective actuator controllers 150 used to drive the DP and IE actuators. The actuator controllers 150 can be configured to drive their respective actuator to a position proportional to an applied analog voltage. In the scenario in which the DP and IE actuators are provided as brushless servomotors, the DP and IE actuators can be controlled by Kollmorgen (VA) AKDO1206 and AKDO0606 servo drives, respectively. The actuator controllers 150 have position, velocity, and current feedback loops coupled with a feed forward gain on position. The gains in the control loops can be set using corresponding tuning software.

Encoders are attached to the DP and IE actuators/servomotors in order to measure their respective angular positions. The position, velocity, and current feedback loops on the actuator controllers can be driven by the corresponding encoder output. The output from the encoders is in volts or is converted to volts, such that analog voltages proportional to the angular positions of the DP and IE actuators/servomotors are transmitted to the DAC. These analog voltages can be scaled such that 1 volt corresponds to a 1° change in angular position of the corresponding DE or IE actuator/servomotor from which the measurement was obtained. The output from these encoders can be used to As mentioned previously, the force plate attached to platform 100 consists of four load cells at the four corners of upper plate 130. The signals/torques from the load cells are processed and transmitted to the DAC or data acquisition system as 8-channel analog signals. The first four signals comprise analog voltages proportional to the normal force acting on each of the load cells, while the next four signals comprise analog voltages proportional to the shear force acting along the four edges of the top face of the force plate.

Muscle activation can be measured using electromyography (EMG) signals. In some embodiments, an EMG measurement apparatus manufactured by Trigno EMG Systems (MA) can be employed. The analog signals transmitted by each EMG sensor are rectified and normalized based on the subject's maximum voluntary contraction (MVC) of the given muscle. The corresponding signals are subsequently used for reflex characterization of the ankle.

Controller Design

Continuing the above example of a PCM 3356 processor, the PCM 3356 processor can be converted into a real-time target machine in order to control platform 100. Real-time control loops can be designed in the Simulink software offered by Mathworks (MA), e.g. the real-time control loops can be exported to the PCM 3356 processor using Simulink Real-Time Explorer. In some embodiments, two actuator controllers 150 can be utilized to collectively define a control system 142 for controlling the platform 100: a position controller 150A and a haptic controller 150B.

The position controller 150A is configured to provide position perturbations to the ankle. Recalling that these position perturbations are utilized to evaluate postural stability and characterize impedance and reflex properties of the ankle in two DOFs, it is desirable that the position controller 150A generate as accurate of position perturbations as is reasonably possible. In order to do so, the position controller 150A generates an analog voltage proportional to the reference input for each of the DP and the IE actuator/servomotor and subsequently transmits this analog voltage to the corresponding servo drive. As mentioned previously, the servo drives have position, velocity, and current feedback control loops with reference feed forward. In some embodiments, one or more of the feedback control loops and/or the servo drives can be tuned using Kollmorgen WorkBench software. The velocity and acceleration limits for each of the DP and IE actuators/servomotors are adjusted based on the required platform response of platform 100. The feedback for the control loops can be obtained from the encoders attached to the servomotors. In some embodiments, the reference for the DP actuator is set at 7281 counts/V and the reference for the IE actuator is set at 4551 counts/V, which corresponds to 1° N in the overall platform 100. With the above-described controller implemented on the real-time target machine, data can be collected (e.g. from the force plate, the encoders, etc.) at 2 kHz, although other collection rates or measurement frequencies may be employed without departing from the scope of the present disclosure.

Figure 2:
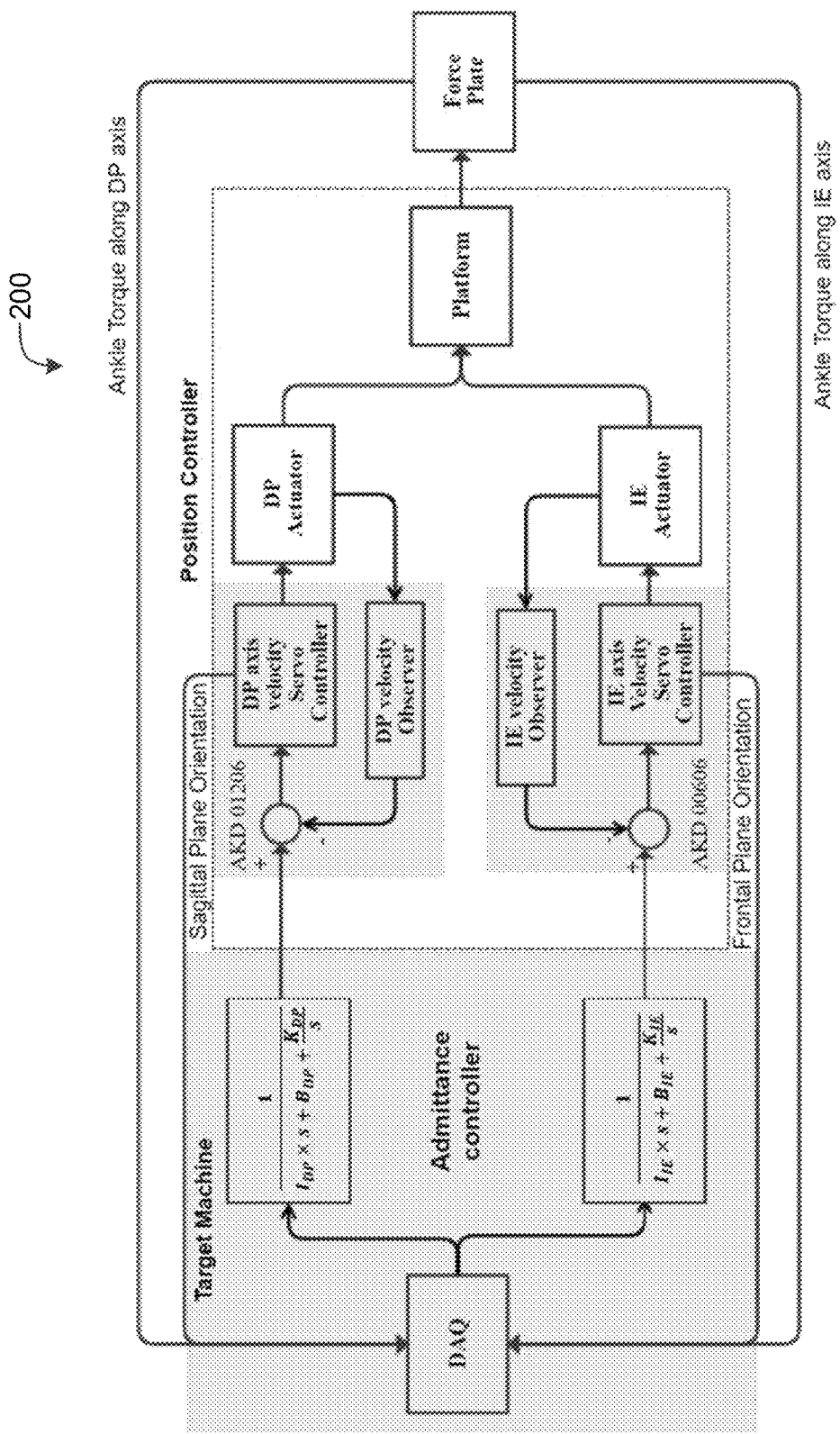
FIG. 2 is a simplified diagram of a haptic controller of a multi-axis robotic platform, according to aspects of the present disclosure.

FIG. 2 depicts an architecture diagram 200 of the haptic controller 150B. As illustrated, the haptic controller 150B is designed based on an admittance control scheme to emulate various mechanical environments on platform 100. Data from the force plate attached to top plate 130 can be used to calculate the torques along the DP and IE axes. The stiffness, damping and inertia of the mechanical environment are simulated to obtain the appropriate deflection of platform 100 along the DP and IE axes, where the appropriate deflection corresponds to the expected real-world response of the environment if the measured torques were to be applied. The position controller 150A is then used to drive platform 100 to the desired position.

Experimental Design

Various capabilities of platform 100 have been experimentally verified. In particular, a series of experiments have validated the capability of the platform to: 1) provide accurate position perturbations to the ankle; 2) emulate a wide range of mechanical environments; 3) estimate ankle impedance; and 4) elicit stretch reflexes of the ankle muscles. The experimental validation holds for both DOFs of the ankle.

For analysis of position controller performance, both slow and fast position perturbations were tested. During postural balance tasks, subjects were expected to experience slow sinusoidal-like oscillatory motions about the ankle axes. To simulate this situation, sinusoidal position perturbations with a frequency between 0.5 Hz and 1 Hz and an amplitude of 8° were utilized. To elicit reflex responses as well as to estimate ankle impedance, platform 100 can be configured to provide fast ramp-and-hold perturbations. Accordingly, fast ramp perturbations of speed 100°/s and 200°/s with an amplitude of 8° were also utilized. In the context of the example and the results discussed below, the accuracy of the position controller was evaluated when a subject of 95 kg was standing on platform 100.

Performance of the haptic controller was evaluated over a wide range of stiffness values from 50 Nm/rad to 1000 Nm/rad that simulated compliant and rigid mechanical environments, respectively. Weights were added in increasing load of 4.5 kg at predetermined positions so as to apply a known amount of torque at the ankle axis. The deflected angular displacement of platform 100 was measured and the corresponding stiffness was calculated.

To demonstrate the ability of platform 100 to accurately estimate ankle impedance, a physical mock up resembling the human ankle was constructed and tested. The stiffness of the mock up was varied by attaching springs of known stiffness. Ramp-and-hold signals of amplitude 3° were used to perturb the mock up ankle from the mean position and the stiffness was calculated based on corresponding torque. The experiment was repeated for a range of stiffness values as follow: 55.80, 107.58, and 171.02 Nm/rad for the DP direction, and 17.88, 55.80, and 107.58 Nm/rad for the IE direction.

To analyze the ability of platform 100 to induce reflex responses, EMG sensors were attached to four major ankle muscles: tibialis anterior, soleus, peroneus longus and medial gastrocnemius. Ramp-and-hold perturbations were applied independently along the DP and IE axes with an amplitude of 8° and at a rate of 200°/s. The perturbations were applied at 10 s intervals, alternating between dorsiflexion and plantarflexion in the sagittal plane and alternating between inversion and eversion in the frontal plane. The reflex responses elicited by the applied perturbations were analyzed by investigating the EMG responses within three time windows relative to perturbation onset: 45-70 ms, 75-95 ms, and 105-135 ms, referred to as the short latency reflex (SLR), medium latency reflex (MLR), and long latency reflex (LLR), respectively.

Results—Position Controller

Figure 3:
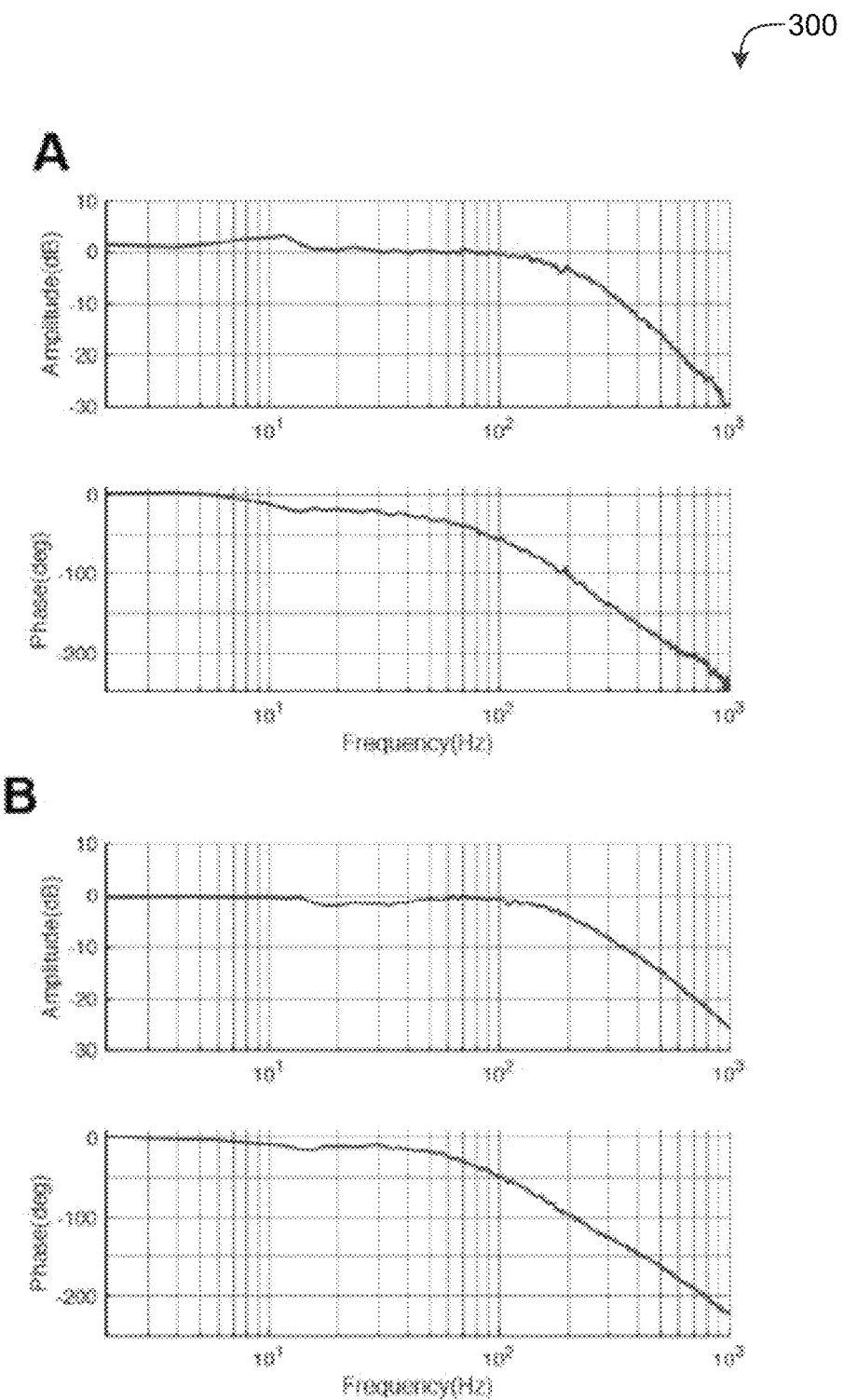
FIG. 3 illustrates closed-loop Bode plots of a servodrive of a multi-axis robotic platform, according to aspects of the present disclosure.

Platform 100 is capable of providing perturbations at a higher frequency than the natural frequency of the ankle. The position bandwidth of the DP and IE actuators was evaluated by their corresponding closed-loop Bode plots, and is around 100 Hz in both DOFs. FIG. 3 depicts these corresponding closed-loop Bode plots 300. In particular, the Bode plots labeled 'A' correspond to the DP actuator/servodrive and the Bode plots labeled 'B' correspond to the IE actuator/servodrive.

Multi-axis robotic platform 100 can provide different types of position perturbations in both DOFs of the ankle with high accuracy even under the loading condition (a subject of 95-100 kg standing on the platform). To test the accuracy of slow position perturbations, sinusoidal waves of the amplitude of 8° were applied to platform 100 at frequencies of 0.5 Hz and 1 Hz. The mean error along the DP and IE axes was less than 0.047° and 0.031°, respectively. These errors are less than 0.3% of the tested range of motion (16°), as seen in Table 1 below.

TABLE 1

Mean and variance of error along both axes for different input signals

| | Direction | | | |
|---|---|---|---|---|
| | DP axis | | IE axis | |
| Input Signal | Mean (deg) | Variance (deg) | Mean (deg) | Variance (deg) |
| 100°/s Ramp | 0.020 | 0.001 | 0.027 | 0.001 |
| 200°/s Ramp | 0.023 | 0.002 | 0.023 | <0.001 |
| 0.5 Hz sinusoid | 0.024 | <0.001 | 0.026 | <0.001 |
| 1 Hz sinusoid | 0.047 | 0.002 | 0.031 | 0.001 |

Figure 4:
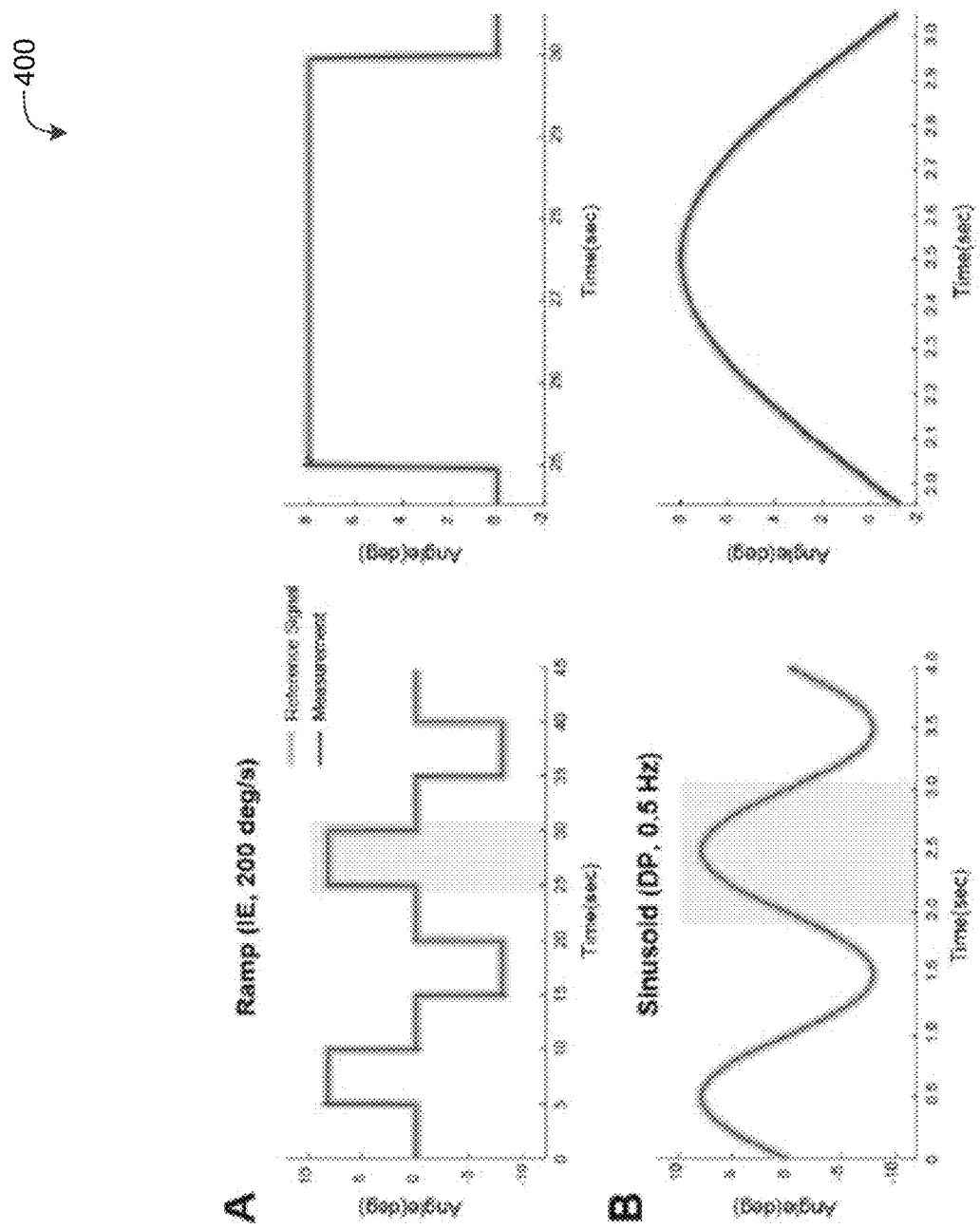
FIG. 4 illustrates sample data of ramp-and-hold and sinusoidal signals applied to a multi-axis robotic platform, according to aspects of the present disclosure.

To test the accuracy of fast position perturbations, rapid ramp-and-hold perturbations with an amplitude of 8° and ramp rates of 100°/s and 200°/s were applied to platform 100. The mean error was less than 0.023° and 0.027° along the DP and IE axes, respectively. These errors correspond to less than 0.2% of the tested range of motion (16°), as can be seen in Table 1 above. Samples of measurements demonstrating the performance of the position controller of platform 100 are illustrated in graph 400 of FIG. 4. In particular, the plots labeled 'A' correspond to a ramp-and-hold signal at a rate of 200°/s in IE, and the plots labeled 'B' correspond to a sinusoidal signal of frequency 0.5 Hz in DP.

Results—Haptic Controller

Figure 5:
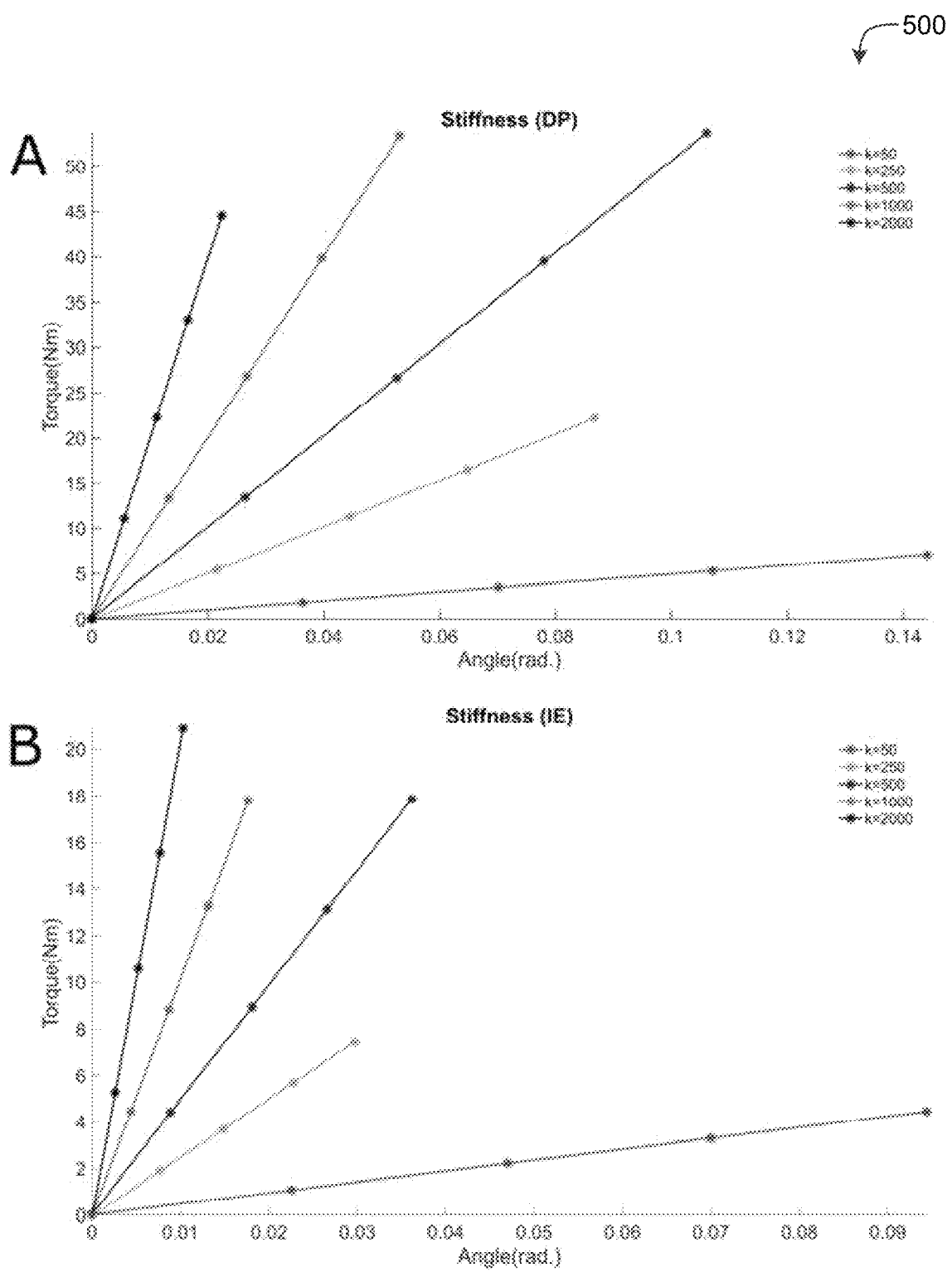
FIG. 5 illustrates stiffness measurements of torques vs. deflection angles for a haptic controller of a multi-axis robotic platform, according to aspects of the present disclosure.

Multi-axis robotic platform 100 can simulate various mechanical (haptic) environments with high accuracy, as can be seen in graphs 500 of FIG. 5. Circles represent measurements (torques vs. deflected angles) using known weights. The slope of the linear fit of measurements was calculated to estimate stiffness of platform 100. Performance of the haptic controller was evaluated by comparing the commanded stiffness of platform 100 and the estimated stiffness using known weights. Stiffness values of 50, 500, and 1000 Nm/rad were tested along both the DP and IE axes. The compliant environment (50 Nm/rad) was simulated with an error of about 1 Nm/rad; for the stiff environments (500 and 1000 Nm/rad), the estimation error increased but the commanded stiffness values were realized with an error of about 1%. These results are summarized below in Table 2:

TABLE 2

Comparison between commanded and measured stiffness of platform 100 for the analysis of the haptic controller

| | Direction | | | |
|---|---|---|---|---|
| | DP axis | | IE axis | |
| Commanded Stiffness (Nm/rad) | Measured Stiffness (Nm/rad) | Error (%) | Measured Stiffness (Nm/rad) | Error (%) |
| 50 | 49.54 | 0.92 | 48.98 | 2.04 |
| 500 | 505.65 | 1.13 | 494.08 | 1.18 |
| 1000 | 1007.5 | 0.75 | 1011.0 | 1.1 |

Results—Stiffness Estimation

It has been demonstrated that multi-axis robotic platform 100 can accurately estimate joint stiffness of the mockup that loosely resembles the human ankle. Stiffness values were estimated with a maximum error of 1.52% and 1.63% along the DP and IE axes, respectively, and the error was reduced with increasing stiffness. These results are summarized below in Table 3:

TABLE 3

Comparison between actual stiffness of ankle mockup and estimated stiffness using multi-axis robotic platform 100

| DP axis | | | IE axis | | |
|---|---|---|---|---|---|
| Theoretical Stiffness (Nm/rad) | Measured Stiffness (Nm/rad) | Error (%) | Theoretical Stiffness (Nm/rad) | Measured Stiffness (Nm/rad) | Error (%) |
| 55.8 | 56.65 | 1.52 | 17.77 | 17.48 | 1.63 |
| 107.58 | 108.15 | 0.52 | 55.80 | 56.66 | 1.54 |
| 171.02 | 170.73 | 0.16 | 107.58 | 107.96 | 0.35 |

Results—Reflex Responses

A pilot test with one human subject confirmed that multi-axis robotic platform 100 can be successfully utilized to elicit reflex responses of the ankle muscles. Sample EMG responses to the rapid ramp-and-hold perturbations are shown in graphs 600 of FIG. 6, which illustrate reflex responses observed in DP (plots 'A') and IE (plots 'B'). In graphs 600, the onset of perturbation is at 0 ms and the reflex responses are observed between 75-150 ms following the onset of perturbation. In other words, while no significant responses were observed in the SLR period (45-70 ms), significant EMG activity was observed both in MLR (75-95 ms) and LLR (105-135 ms) periods.

Testing

Two chronic stroke survivors (age: 54-60, weight: 60-65 kg) and two relapsing and remitting MS patients (age: 49-50, weight: 63-81 kg) participated in this pilot study. All subjects were affected on their right leg. In addition, three healthy subjects (age: 23-31, weight: 56-71 kg) were recruited to serve as a reference. This study was approved by the Institutional Review Board of Arizona State University and all experiments were performed after informed consent of the subjects.

Figure 7:
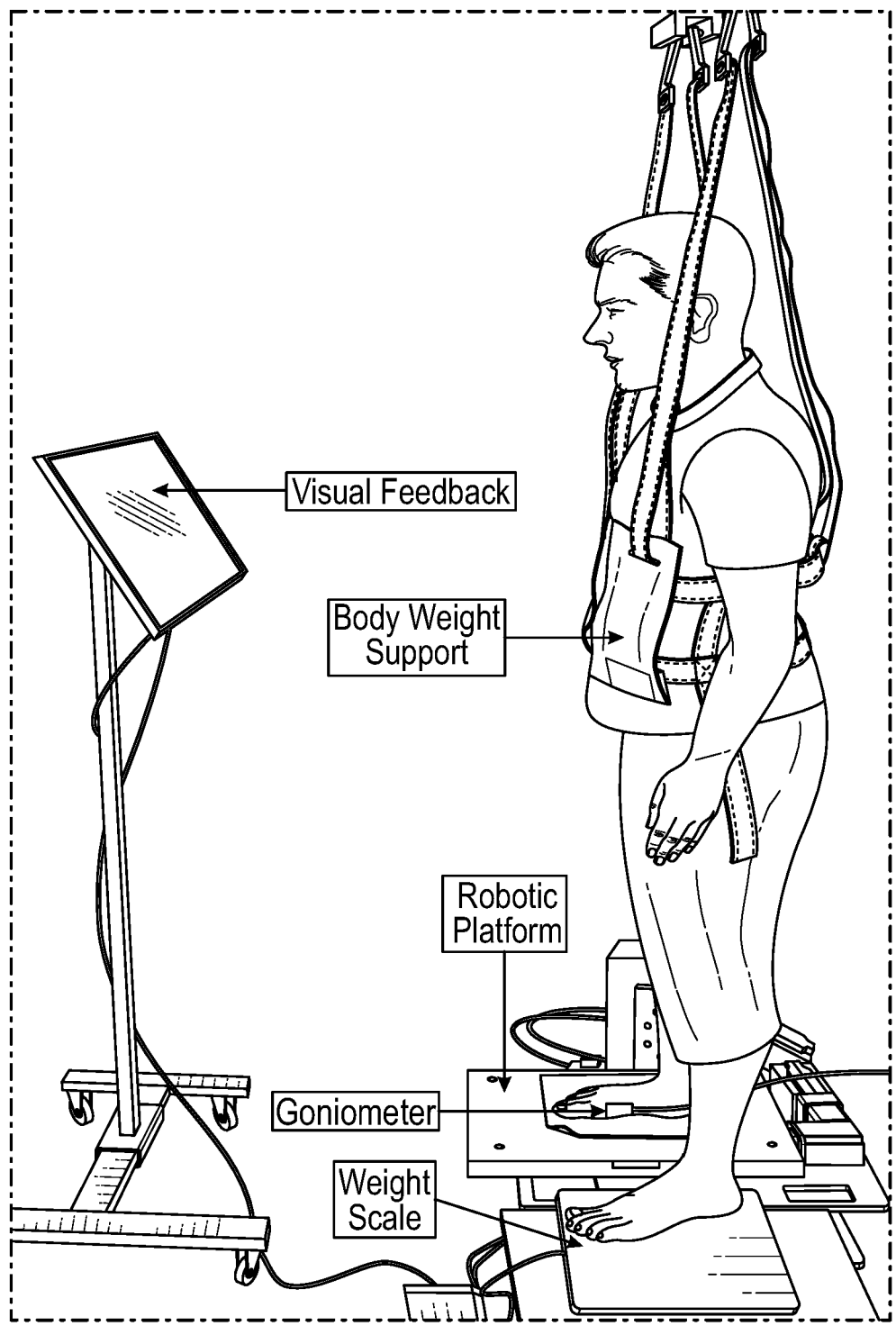
FIG. 7 is an image showing the experimental setup for testing the multi-axis robotic platform, according to aspects of the present disclosure.

The multi-axis robotic platform 100 was utilized to quantify stiffness and damping components of the ankle mechanics during upright standing in 2 degree-of-freedom (DOF) of the ankle, specifically, dorsiflexion-plantarflexion (DP) and inversion-eversion (IE) [2] (FIG. 7).

Each subject was instructed to stand upright with the right foot (affected side) on the robotic platform and the left foot on the weight scale, which was used to ensure equal weight distribution between legs. A dual-axis goniometer was attached to the subject's ankle to measure ankle angles in 2 DOFs. To encourage the subject to maintain the same upright posture, visual feedback was used, which displayed real-time center-of-pressure location in 2 DOFs as well as weight distribution between legs.

Once the subject maintained upright posture, ramp perturbations (amplitude: 3°, speed: 40°/s) were applied to the ankle in one of the four directions in random order: dorsiflexion, plantarflexion, inversion, and eversion. Ten repeated trials were completed for each perturbation direction.

Ankle stiffness and damping parameters in each DOF were quantified by fitting a $2^{nd}$ order model (consisting of ankle stiffness, ankle damping, and foot inertia) to the measured kinematics and torques at the ankle. Reliability of quantification was evaluated by calculating the percentage variance accounted for (% VAF) between the measured ankle torques and estimated ankle torques from the best-fit $2^{nd}$ order model.

In all stroke and MS subjects, the reliability for the characterization of ankle mechanics, i.e., % VAF, was higher than 98% in both DOF of the ankle and in any perturbation directions. This high reliability with a $2^{nd}$ order model demonstrated that even altered ankle mechanics in stroke and MS patients could be accurately quantified by ankle stiffness and ankle damping parameters as in healthy subjects.

Figure 8:
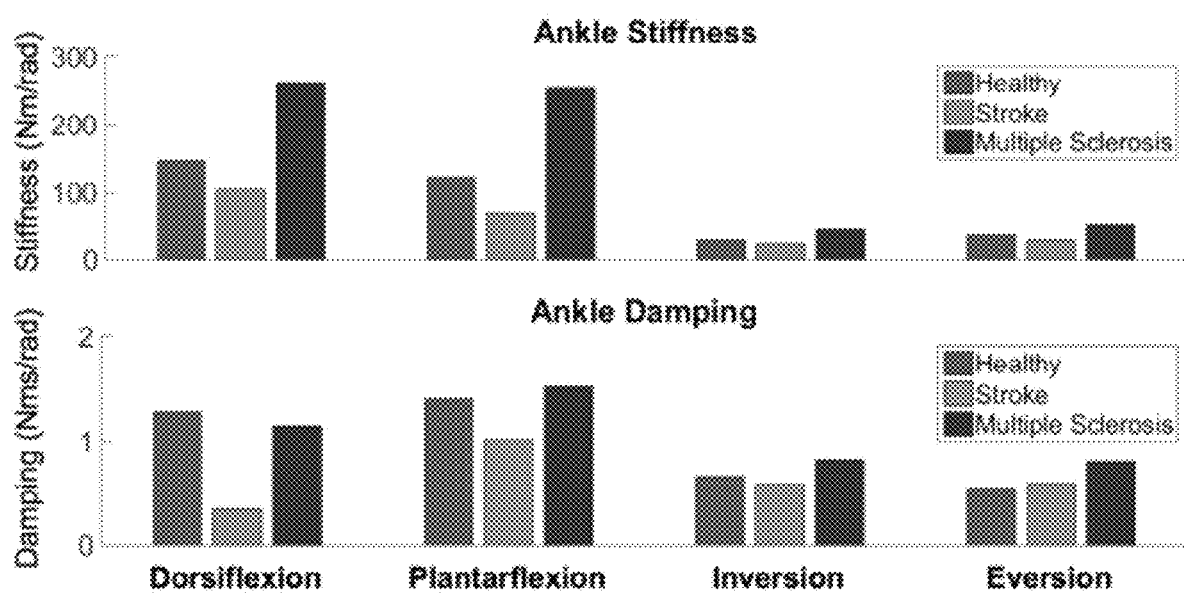
FIG. 8 is a graphical representation showing the comparison of ankle stiffness and damping of healthy, stroke and MS subjects, according to aspects of the present disclosure.

Ankle stiffness and damping in DP (DP stiffness and damping) of both stroke subjects were lower than those of healthy subjects (FIG. 8). In particular, DP stiffness of the first stroke subject was 2~3 times lower than the healthy human stiffness (Table 4). Lower DP stiffness and damping could explain the prevalence of drop foot in stroke survivors.

Ankle stiffness in IE (IE stiffness) of both stroke subjects was lower than that of healthy subjects. However, the difference in IE stiffness between groups (stroke vs. healthy) was much smaller than DP stiffness. Ankle damping in IE (IE damping) was comparable to that of healthy subjects (Table 4).

Contrary to the results in stroke subjects, DP stiffness of both MS subjects was higher than that of healthy subjects. In average, DP stiffness of MS subjects was about 2 times higher than the healthy human stiffness. This result may be due to higher spasticity and/or altered passive muscle properties in MS patients. DP damping of MS subjects was comparable to that of healthy subjects (Table 4).

TABLE 4

Comparison of ankle stiffness and damping between healthy, stroke, and MS subjects.

| | Dorsiflexion | | Plantarflexion | | Inversion | | Eversion | |
|---|---|---|---|---|---|---|---|---|
| Subject | Stiffness Nm/rad | Damping Nms/rad | Stiffness Nm/rad | Damping Nms/rad | Stiffness Nm/rad | Damping Nms/rad | Stiffness Nm/rad | Damping Nms/rad |
| Healthy | 147.99 | 1.27 | 121.53 | 1.41 | 29.23 | 0.66 | 37.20 | 0.54 |
| Stroke 1 | 77.44 | 0.31 | 45.56 | 1.07 | 24.22 | 0.65 | 27.96 | 0.64 |
| Stroke 2 | 132.45 | 0.41 | 91.95 | 0.95 | 25.12 | 0.51 | 31.38 | 0.55 |
| MS 1 | 325.13 | 1.51 | 294.96 | 1.65 | 55.57 | 0.97 | 65.23 | 0.93 |
| MS 2 | 198.22 | 0.77 | 211.54 | 1.39 | 35.65 | 0.67 | 40.23 | 0.68 |

Both MS subjects exhibited higher IE stiffness and damping than those of healthy subjects. However, the difference in IE stiffness between groups was much smaller than DP stiffness (Table 4).

This study demonstrated that a robotic approach based on a multi-axis robotic platform 100 could be reliably used for the quantification of altered ankle mechanics in 2 DOFs in stroke and MS patients, evidenced by the high reliability measure in all experimental conditions.

This study also confirmed that altered ankle mechanics during upright standing are highly dependent on the type of neurological disorder. In addition, according to the results of this pilot study, both stroke and MS have higher impact on the alteration of ankle mechanics along DP in the sagittal plane than IE in the frontal plane.

Findings in this study support the need for individual characterization of altered ankle mechanics in order to deliver optimal patient-specific rehabilitation services. For example, the MS subjects in this study would need stretching exercises to increase joint flexibility, while the stroke subjects would need strengthening exercises to reduce weakness at the ankle joint.

Results

Disclosed herein is a novel multi-axis robotic platform 100 for the characterization of ankle neuromechanics (mechanical impedance and reflex responses) in the sagittal (DP) and frontal (IE) planes. Platform 100 provides unique functionalities, not available in conventional devices to study the ankle, including exoskeletons and active orthoses.

Figure 6:
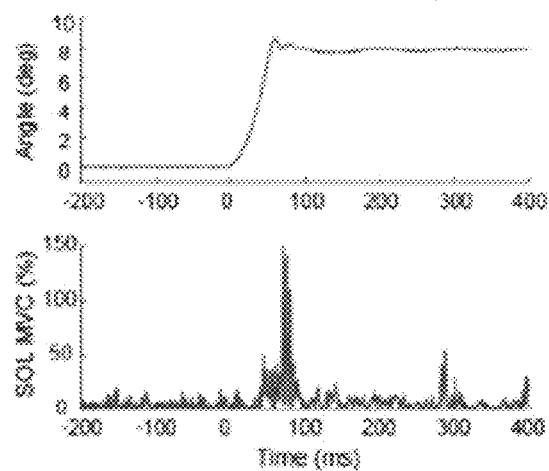
FIG. 6 illustrates reflex responses to perturbations of a multi-axis robotic platform, according to aspects of the present disclosure.
Figure 6:
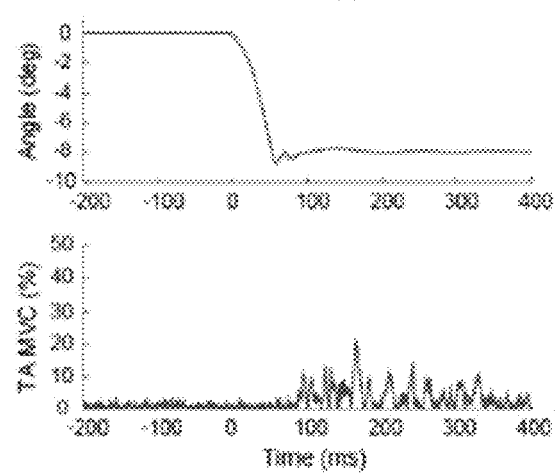
Figure 6:
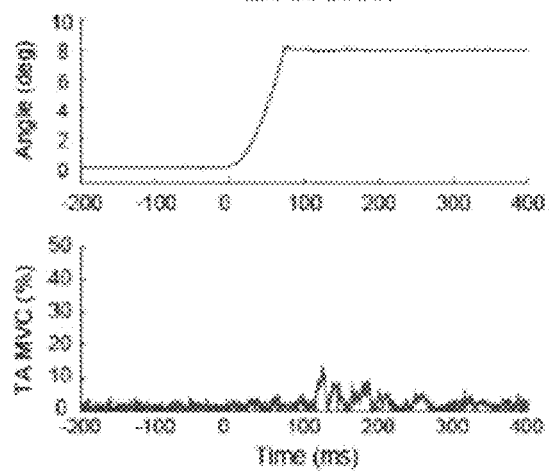
Figure 6:
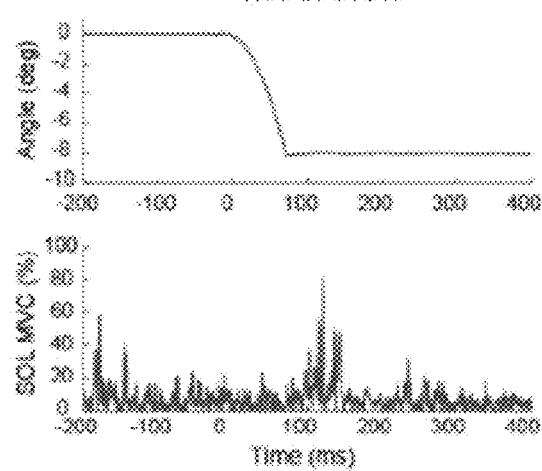

Multi-axis robotic platform 100 allows for a wide range of ankle motions (30° and 20° for DP and IE, respectively), and can support a subject of weight 100 kg by providing strong torques along both DP and IE axes. Platform 100 can be recessed into an elevated walkway with a height of 200 mm, which can permit an easier performance of various lower-extremity studies, including postural balance and locomotion tasks. The bandwidth of multi-axis robotic platform 100 can be 100 Hz or greater, much higher than the natural frequency of the ankle. Accordingly, high accuracy of the position controller can be achieved for different types of perturbations; platform 100 can provide rapid perturbations in both DOFs up to 200°/sec with an error less than 0.05°. This rapid perturbation is an important requirement to investigate reflex responses of the ankle muscles, as can be seen in FIG. 6, and is additionally an important factor in separating the contributions of intrinsic and reflexive components of the ankle impedance. In addition, the haptic controller can successfully simulate a wide range of haptic environments, from compliant to rigid, with an error of 2% of the commanded values.

The disclosed multi-axis robotic platform 100 provides unique functions to realize realistic mechanical environments that are encountered in many functional tasks. Platform 100 is able to switch between the position control mode and the haptic control mode within 0.5 ms, which can be advantageous in seamlessly simulating realistic mechanical environments and transiently perturbing the ankle to characterize its neuromuscular properties.

Multi-axis robotic platform 100 can be utilized in a variety of dynamic functional tasks including posture maintenance and locomotion. Quantitative characterization of mechanical impedance and reflex responses of the ankle during dynamic functional tasks can provide an important guideline for the design and control of lower-extremity wearable robots, including active ankle-foot orthoses, powered prosthesis, and exoskeletons. For example, quantitative information of mechanical impedance could help design a robotic controller to optimize the trade-off between stability and performance.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A multi-axis robotic platform comprising:
   a bottom plate;
   a top plate positioned over the bottom plate, the top plate including a support surface for receiving an ankle;
   a middle plate, movably coupled between the bottom plate and the top plate;
   a first actuator positioned along the bottom plate and connected to the middle plate via a first coupling such that a shaft of the first actuator rotates the middle plate along a dorsiflexion-plantarflexion (DP) axis of the ankle;
   a second actuator positioned along the middle plate and connected to the top plate via a second coupling such that a shaft of the second actuator rotates the top plate along an inversion-eversion (IE) axis of the ankle; and
   a control system for controlling the first actuator and the second actuator, the control system operable to switch between a position control mode and a haptic control mode to simulate realistic mechanical environments and transiently perturb the ankle to characterize its neuromuscular properties.

2. The multi-axis robotic platform of claim 1, wherein the first coupling:
   prevents transverse loading of the shaft of the first actuator.

3. The multi-axis robotic platform of claim 2, wherein the first coupling is a flexible coupling.

4. The multi-axis robotic platform of claim 1, wherein the second coupling:
   prevents transverse loading of the shaft of the second actuator.

5. The multi-axis robotic platform of claim 4, wherein the second coupling is a high-speed rigid coupling.

6. The multi-axis robotic platform of claim 1, wherein the control system actuates one or more of the first actuator and the second actuator to move the ankle in two degrees-of-freedom (DOFs).

7. The multi-axis robotic platform of claim 6, wherein the control system determines a mechanical impedance of the ankle and reflex characteristics of the ankle based at least in part on one or more force measurements obtained in response to moving the ankle.

8. The multi-axis robotic platform of claim 7, further comprising one or more electromyography (EMG) sensors attached to the ankle, wherein the control system determines the reflex characteristics of the ankle based at least in part on EMG data measured by the EMG sensors.

9. The multi-axis robotic platform of claim 6, wherein the control system comprises at least a position controller and a haptic controller for generating control signals for one or more of the first actuator and the second actuator.

10. The multi-axis robotic platform of claim 9, wherein the haptic controller emulates one or more mechanical properties of a desired environment for the ankle.

11. The multi-axis robotic platform of claim 10, wherein the haptic controller calculates stiffness, damping, and inertia of the desired environment to thereby determine corresponding deflections along the DP and IE axes.

12. The multi-axis robotic platform of claim 11, wherein the position controller generates the control signals and drives the middle plate and the top plate to achieve the corresponding deflections along the DP and IE axes.

13. The multi-axis robotic platform of claim 9, wherein the position controller generates the control signals and applies positional perturbations to the ankle, wherein the positional perturbations are generated using one or more of the first actuator and the second actuator.

14. The multi-axis robotic platform of claim 13, wherein the positional perturbations comprise one or more of ramp-and-hold perturbations and sinusoidal perturbations.

15. The multi-axis robotic platform of claim 1, wherein one or more of the first actuator and the second actuator comprise a brushless servomotor.

* * * * *